US010878952B1

(12) United States Patent
Patel et al.

(10) Patent No.: US 10,878,952 B1
(45) Date of Patent: Dec. 29, 2020

(54) SYSTEM AND METHOD FOR EXERCISE TRACKING

(71) Applicants: Shamik Sunil Patel, Los Altos Hills, CA (US); Ruehanee Killer Patel, Los Altos Hills, CA (US); Gokulesh Killer, Los Altos Hills, CA (US)

(72) Inventors: Shamik Sunil Patel, Los Altos Hills, CA (US); Ruehanee Killer Patel, Los Altos Hills, CA (US); Gokulesh Killer, Los Altos Hills, CA (US)

( * ) Notice: Subject to any disclaimer, the term of this patent is extended or adjusted under 35 U.S.C. 154(b) by 0 days.

(21) Appl. No.: 15/809,822

(22) Filed: Nov. 10, 2017

(51) Int. Cl.
| | |
|---|---|
| G06F 17/00 | (2019.01) |
| G16H 20/30 | (2018.01) |
| G06K 7/10 | (2006.01) |
| A63B 24/00 | (2006.01) |
| A63B 71/06 | (2006.01) |
| H04W 4/80 | (2018.01) |
| A63B 21/072 | (2006.01) |

(52) U.S. Cl.
CPC ......... *G16H 20/30* (2018.01); *A63B 24/0062* (2013.01); *A63B 71/0622* (2013.01); *G06K 7/10297* (2013.01); *G06K 7/10396* (2013.01); *A63B 21/0724* (2013.01); *A63B 2024/0071* (2013.01); *A63B 2071/0625* (2013.01); *A63B 2220/12* (2013.01); *A63B 2220/17* (2013.01); *A63B 2220/62* (2013.01); *A63B 2220/73* (2013.01); *A63B 2220/803* (2013.01); *A63B 2220/808* (2013.01); *A63B 2220/833* (2013.01); *A63B 2220/836* (2013.01); *A63B 2225/50* (2013.01); *A63B 2225/54* (2013.01); *H04W 4/80* (2018.02)

(58) Field of Classification Search
CPC ....... G06Q 30/02; G07F 7/1008; G06K 17/00
USPC .......................................... 235/375
See application file for complete search history.

(56) References Cited

U.S. PATENT DOCUMENTS

| | | | |
|---|---|---|---|
| 9,135,347 B2 | 9/2015 | Damman | |
| 9,844,032 B2* | 12/2017 | Johnson | ................ H04W 72/04 |
| 2003/0216228 A1 | 11/2003 | Rast | |
| 2006/0117458 A1 | 6/2006 | Ishihara | |
| 2008/0090703 A1* | 4/2008 | Rosenberg | ............. A63B 24/00 482/8 |
| 2008/0170123 A1* | 7/2008 | Albertson | .......... A63B 24/0003 348/157 |
| 2009/0149299 A1 | 6/2009 | Tchao | |

(Continued)

*Primary Examiner* — Ahshik Kim
(74) *Attorney, Agent, or Firm* — Law Office of Michael O'Brien; Michael J. O'Brien

(57) ABSTRACT

An apparatus, system and method for exercise tracking that comprises at least one mother unit, equipment tag, base unit, and RF user tag. The mother unit comprises equipment tag reader and sensor and is joined to an equipment in a gym. The tag is placed on the equipment and in communication with the mother unit. The base unit comprises a RFID reader. A plurality of mother units is in communication with the base unit. The RF and GPS enabled user tag is provided and joined to user in gym and in communication with the mother unit. The apparatus is a substantially hands-free. User profile and user exercise data is captured. A computer system in communication with the base unit is provided. Data captured by the mother unit is communicated to and analyzed by the computer system, and feedback communicated to the mother unit is communicated to user.

19 Claims, 11 Drawing Sheets

(56) References Cited

U.S. PATENT DOCUMENTS

| | | |
|---|---|---|
| 2010/0167876 A1 | 7/2010 | Cheng |
| 2010/0317488 A1 | 12/2010 | Cartaya |
| 2011/0165997 A1 | 7/2011 | Reich |
| 2013/0135115 A1* | 5/2013 | Johnson ................ G08C 19/00 340/870.02 |
| 2013/0209972 A1* | 8/2013 | Carter ................ G09B 19/0092 434/127 |
| 2014/0135593 A1 | 5/2014 | Jayalth |
| 2014/0194250 A1 | 7/2014 | Reich |
| 2014/0336947 A1 | 11/2014 | Walke |
| 2015/0057128 A1 | 2/2015 | Ishii |
| 2015/0170530 A1 | 6/2015 | Damman |
| 2015/0265903 A1 | 9/2015 | Kolen |
| 2016/0023043 A1 | 1/2016 | Grundy |
| 2016/0101320 A1 | 4/2016 | Tsutsui |
| 2016/0292509 A1 | 10/2016 | Kaps |
| 2016/0337843 A1 | 11/2016 | Repka |
| 2018/0117417 A1 | 5/2018 | Davis |
| 2018/0156657 A1 | 6/2018 | Lee |

\* cited by examiner

US 10,878,952 B1

SYSTEM AND METHOD FOR EXERCISE TRACKING

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to a system and method for tracking exercise activities. More particularly, certain embodiments of the invention relate to a substantially hands-free and substantially automated system and method for tracking exercise activities.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Exercise and activity trackers and analyzers have increasing become a popular way for a person to gauge his/her health status. The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that typically most exercise tracker devices, systems and methods available in the market may require considerable data input from a user before and during the exercise schedule. It is believed that some of the devices may require a user to pre-program the user's gym routine on their web portal before going to the gym. The device may at times require the user to synchronize their device to a portal in order for the device to know in advance what activity the user may be performing. The device in turn may then start tracking the user's activity. The user may not be in a position to improvise upon or change the pre-programmed activity spontaneously.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
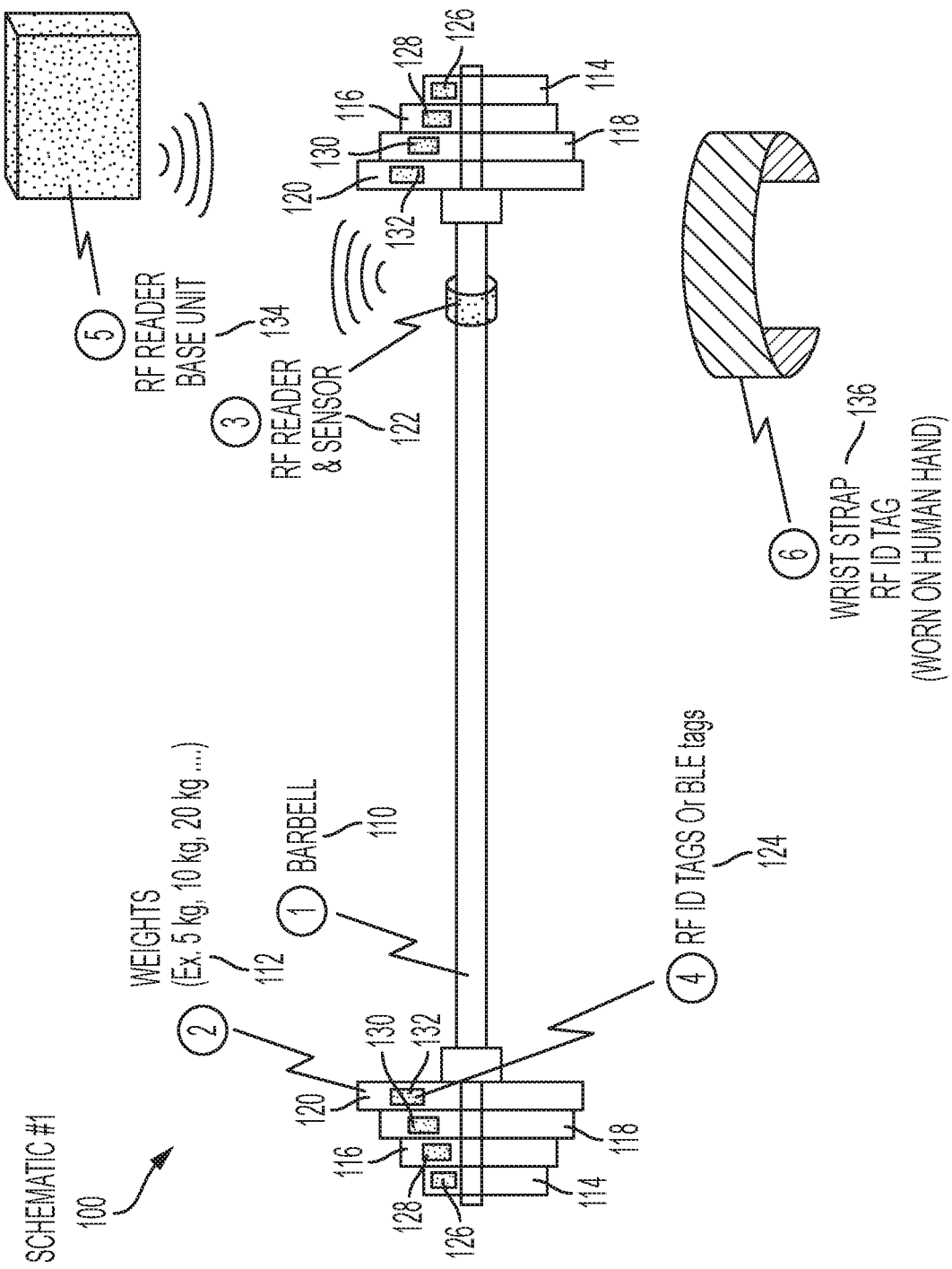
FIG. 1 illustrates an exemplary exercise tracker system, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognized in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit "about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v. Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s)/way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of. or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically, a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.).

Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Additionally, the phrase "configured to" or "operable for" can include generic structure (e.g., generic circuitry) that is manipulated by software and/or firmware (e.g., an FPGA or a general-purpose processor executing software) to operate in a manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

In one embodiment, is provided an exercise tracker system. In one embodiment, the exercise tracker system may include an indirect wearable. The exercise tracker system may capture details of all gym activities, including but not limited to, weight lifting activities, automatically using minimal input from a user. In one embodiment, the input may be a hands-free input i.e., a voice input from the user. In another embodiment, the input may be a tap input, for example, a one touch or tap input from the user.

In one embodiment, the exercise tracker system and method of the present invention provide a user with automated tracking of exercises performed in gymnasium (hereinafter at times referred to as gym). In one embodiment, the user may also be enabled to automatically track the weights they use, the repetitions made, and number of sets of weights used, the total time they used and total rest time.

In one embodiment, the exercise tracker system may include four components, including, but not limited to, (i) a radio frequency (RF) reader and sensor; (ii) a tag for an equipment, for example, a radio frequency identification tag (RF ID), a short range wireless interconnection tag, i.e., a bluetooth beacon or a BLE Tag, or a combination thereof; (iii) a RF reader base unit; and (iv) an RF ID tag wearable for a user. The first component, i.e., the RF reader and sensor may at times to referred to as the mother unit. Referring to FIG. 1, is illustrated an exemplary exercise tracker system, in accordance with an embodiment of the present invention. FIG. 1 illustrates an exemplary embodiment of tracking the exercise routine of a user using a barbell 110. In the exemplary embodiment, shown in FIG. 1, the barbell is shown to have a set of weights 112, for example, the bar bell may include weights 5 kg, 114, 10 kg 116, 20 kg 118, and 30 kg 120. In one embodiment, a first component, i.e., RF ID reader and sensor 122 may be placed at a convenient location on the bar bell, for example, as shown in FIG. 1. In one embodiment, a second component, i.e., a tag for an equipment 112 may be placed on the set of weights, for example, one tag each, i.e., 126, 128, 130, and 132 may be respectively placed on each weight 5 kg, 114, 10 kg 116, 20 kg 118, and 30 kg 120 on each side of the bar bell 110. In one embodiment, a third component, i.e., a RF reader base unit 134 may be placed in proximity to the first component, i.e., the RF ID reader and sensor 122. It may be appreciated by a person with ordinary skill in the art, in light of and in accordance with the teachings of the present invention, that the RF reader base unit 134 may be placed at a distance sufficient to receive and send RF signals to the RF ID reader and sensor 122. In one embodiment, the RF reader base unit 134 may be placed on a wall. In one embodiment, the fourth component, i.e., a RF ID tag wearable may be provided to a user. It may be appreciated by a person with ordinary skill in the art, in light of and in accordance with the teachings of the present invention, that the RF ID tag wearable 134 may be designed and worn in any manner convenient to the user. In one embodiment, the wearable is in the form of a wrist band.

In one exemplary embodiment, when the equipment used for exercising is a bar bell 110 as shown in FIG. 1, two components i.e., the first component, RF ID reader and sensor 122 and the second component, tags 112 may focus on tracking the weights, repetitions, and sets. The first and second components may be placed directly on the equipment itself. It may be appreciated by a person with ordinary skill in the art, in light of and in accordance with the teachings of the present invention, that the first and second components may be placed in locations close enough to each other, which enables them to communicate with each other and transmit data. Further, the placement of the two components may provide an accurate reading of the weights being used. In one embodiment, the first and second components may be permanently located on the equipment. They may not require removal and re-placement every time a user needs to use the equipment. In one embodiment, the first and second components may not be in the control of the user who is exercising or doing his/her routine.

It may be appreciated by a person with ordinary skill in the art, in light of and in accordance with the teachings of the present invention, that the invention disclosed herein may be a substantially hands-free exercise tracker system and method. Accordingly, the first and second components may not require any excessive manual tactile input by the user, for example, addition of user details, pre-program a gym routine before workout, number punching, store pre-determined information, provide data while working out, and the like. In one embodiment, the exercise tracker system described herein enables a user do their exercises without worrying about keeping a "diary" or carry a compatible mobile device to track their exercise routine, for example, weights, repetitions, and sets in the case of bar bell. In one embodiment, the exercise tracker system disclosed herein may require a voice input. In one embodiment, the voice input may be in the form of a user's voice or a voice produced by the user tapping on the wearable. This is advantageous as it allows the user to have his/her hands free for weight lifting.

In one embodiment, the four components i.e., (i) a RF reader and sensor; (ii) a tag for equipment; (iii) a RF reader base unit; and (iv) an RF ID tag wearable for a user; may communicate with each other via RF and wireless communications.

In one embodiment, the exercise tracker system may not need an external communication device, i.e., a mobile device like a hand held, smart phone, pad, etc. . . . to control the exercise tracker system. In one embodiment, the exercise tracker system and method may include a designated computer program. In one embodiment, the exercise tracker system may not require a connected user interface to manipulate its functions since the user does not need to provide extensive manual input other than a voice/tap input as described hereinabove.

In one embodiment, the first component, i.e., the RF reader and sensor 122 may include a voice activated feature. In one embodiment, the RF reader and sensor 122 may include a built in microphone and speaker i.e., the RF reader and sensor 122 may be capable of receiving a voice input and may be capable of providing a voice output, for example, projecting a message. In one embodiment, the wearable may include RF ID tags that may be associated with the wearable.

Figure 2:
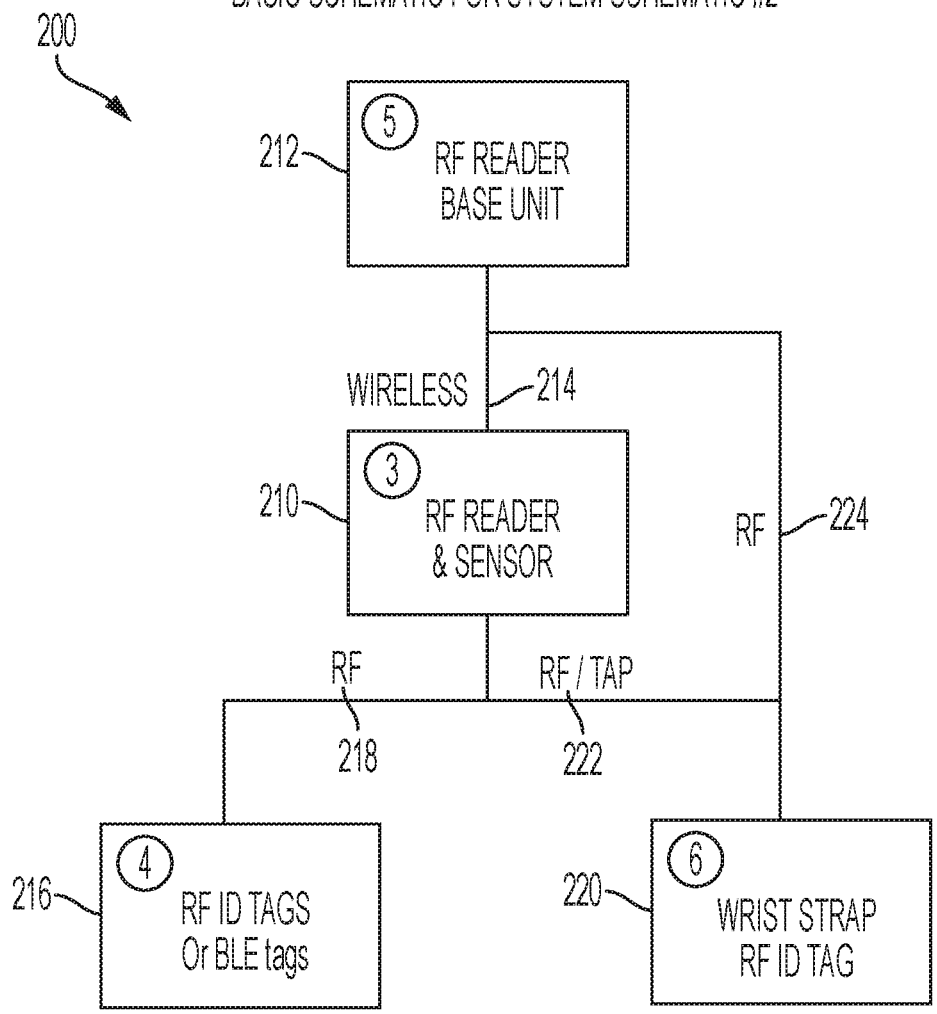
FIG. 2 is a block diagram illustrating communication between the components in an exemplary exercise tracker system, in accordance with an embodiment of the present invention.

In one embodiment, the a RF reader base unit may be in communication with the RF ID tags in the wearable and the first component i.e., the RF ID reader and sensor. In one embodiment, the base unit may communicate with the RF ID tags and the mother unit via RF connectivity/Bluetooth/ Wireless Connectivity. Referring to FIG. 2 is illustrated a block diagram 200 showing the communication between the components an exemplary exercise tracker system, in accordance with an embodiment of the present invention. FIG. 2 illustrates the communication system between the four components described herein above. In one exemplary embodiment, as shown in FIG. 2, the RF reader and sensor 210 may communicate 214 with the RF reader base unit 212 via a wireless communication. The RF reader and sensor 210 may communicate 218 with tags 216 on the equipment via RF or Bluetooth®. The RF reader and sensor 210 may communicate 222 with the wearable 220 via RF. In one embodiment, the RF reader and sensor 210 may communicate 222 with the wearable 220 via a "TAP". In this embodiment, the RF reader and sensor 210 may include a designated computer program that may enable the RF reader and sensor 210 to read a "User ID" programmed into the RF ID tag(s) in the wearable, with a "TAP" made by the user on the wearable RF ID. The "TAP" function may include a modified proximity sensor. The RF reader and sensor 210 may detect/ acknowledge the RF ID tag in the wearable only when the RF ID tag in the wearable is a in a "TAP" proximity to the RF reader and sensor 210. In one embodiment, the RF ID reader and sensor 210, the tags for equipment 216, and the RF ID tag in the wearable 220 may communicate with each other via RF and Bluetooth®. In one embodiment, the RF ID tag in the wearable may communicate with the RF reader base unit to activate a user's profile. The RF ID tag in the wearable 220 may communicate 224 with the RF reader base unit 212 using RF or GPS. For example, the RF reader base unit 212 may include a designated computer program that may be capable of reading the user ID form the RF ID tag in the wearable 220. When the user is given the wearable, for example, at the reception desk of the gym, the RF reader base unit 212 may acknowledge the activation of the RF ID tag in the wearable 220 given to the user, and prompt the RF reader base unit 212 may be prompted by the designated computer program to activate the profile of the user.

Figure 3:
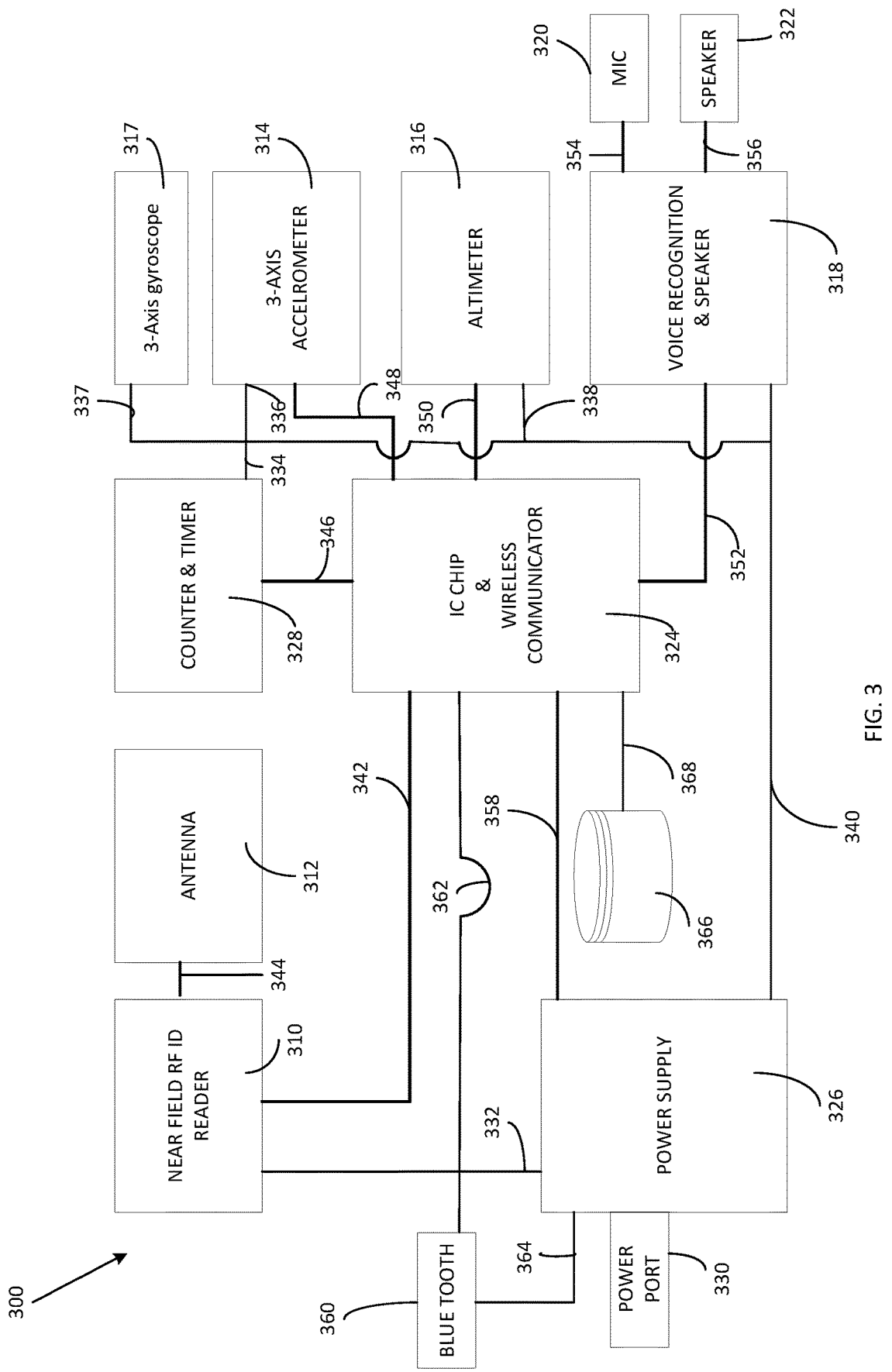
FIG. 3 is a block diagram illustrating a component of an exemplary exercise tracker system, in accordance with an embodiment of the present invention.

Referring to FIG. 3 is illustrated a block diagram 300 of one component of an exemplary exercise tracker system, in accordance with an embodiment of the present invention. FIG. 3 illustrates the sub-components of the RF reader and sensor 300. In one embodiment, the RF reader and sensor 300 may include an RF ID reader 310, an antenna 312, an 3-axis accelerometer 314, an altimeter 316, an 3-axis gyroscope 317, voice recognition hardware 318; a microphone 320, a speaker 322, an integrated circuit (IC chip) and wireless communicator 324, a bluetooth module 360, a power source 326, and a counter/timer 328. In one embodiment, as shown in FIG. 3, the IC chip and wireless communicator 324 may be encompassed in one chip. In another embodiment, the IC chip and wireless communicator 324 may include two separate chips. The function of each of the sub-component may be as listed herein. The RF ID reader 310 may include a near field RF ID reader that may read nearby RF ID tags attached to an equipment or RF ID tags present in a wearable. The RF ID reader 310 may include a near field Bluetooth® (BLE) reader that may read nearby BLE tags attached to an equipment. In one embodiment, when the equipment may be a bar bell, as shown in FIG. 1, the RF ID reader 310 may identify the weights/sets connected to the bar bell. The antenna 312 may be used to supply power to the tags attached to an equipment or RF ID tags present in a wearable. The 3-axis accelerometer 314 may be used to measure the motion characteristics of the equipment i.e., the velocity, direction, speed, movement, and the like. The altimeter 316 may be used to measure the altitude of the equipment to identify the exercise being performed. The 3-axis gyroscope 314 may be used to measure the rotational motion characteristics of the equipment i.e., orientation, direction, speed, movement, and the like. The voice recognition hardware 318 may be used to receive the voice input (command) provided by the user and decipher the voice input. The microphone 320 may be used for voice input and the speaker 322 may be used for voice output. The IC chip 324 may be used to connect all above sub-components and coordinate all information before sending the base unit. The power source may be used to powers all internal components. The power supply may include but is not limited to a power supply port 330 or a battery. The timer 328 may be used synchronously with the 3-axis accelerometer, and 3-axis gyroscope, and altimeter to track the exercise and repetition speed, set counter, set timer, etc. . . . The timer may also be used for power saving mode, i.e., idle time determination, switch ON/switch OFF operation, etc. . . .

As shown in FIG. 3 the power supply 326 may provide power supply 332 to the RF ID reader 310, power supply 334 to the timer 328; power supply 336 to the 3-Axis accelerometer 314; power supply 337 to the 3-axis gyroscope 317; power supply 338 to the altimeter 316; power supply 340 to the voice recognition hardware 318, power supply 364 to the Bluetooth module 360, and power supply 358 to the IC chip and wireless communicator 324. The IC chip and wireless communicator 324 controls the sub-components via its connection to the sub-components; connection 342 for RF ID reader 310, the antenna 312 is connected 344 to the RF ID reader 310, connection 346 for timer 328, connection 348 for 3-axis accelerometer, connection 352 for altimeter 316, connection 352 for voice recognition hardware 318, the microphone 320 is connected 354 with the voice recognition hardware 318, and the speaker 322 is connected 356 with the voice recognition hardware 318. In certain embodiments, the RF reader and sensor 300 may be enabled with Bluetooth® 360 connected 362 to the IC chip and wireless communicator 324. The RF reader and sensor may also include a database 366, that may receive data from the IC chip and wireless communicator 324 and the data may be stored in the database 366.

In one embodiment, the tags for the equipment may include an active BLE tag or a passive RF ID tag. It may be appreciated by a person with ordinary skill in the art, in light of and in accordance with the teachings of the present invention, that the RF ID tags may include a transponder, or radio transmitter receiver, that may be activated when it receives a predetermined RF signal. In an exemplary embodiment, where the equipment is a bar bell as shown in FIG. 1, the tag 124 may include information on the specific weight it is affixed to. The tag 124 may also have an antenna that may receive power supply from the RF reader and sensor 122. In one embodiment, the tag may be affixed to the equipment using a multi-surface adhesive. The multi-surface adhesive may enable the tags 124 to be affixed to any surface including, but not limited to, metals, rubber, polymer, fabric, and the like. In certain embodiments, the tags may be embedded into the equipments or the wearable during manufacturing. In one embodiment, the tags may include active tags. In the embodiment, where the tags are active, the tags may be charged wirelessly by either by the RF reader base unit or by the RF reader and sensor i.e., the mother unit. In an alternative embodiment, the active tags may have a separate charging station connected to a power supply. In an alternative embodiment, the active tags may have a solid state battery/rechargeable battery as a power supply and may be connected to a power supply for charging the solid state battery. In one embodiment, all equipments may be kept in proximity of a central charger that may wirelessly charge the tags attached to them.

In one embodiment, the wearable 136, for example, the RF ID tag wrist band for the user may include a passive RF ID tag. The wearable 136 may contain user information that can be re-programmed for a different user every time it is worn, for example, like a hotel key. In one embodiment, the RF ID tags in the wearable may include active RF ID tags. In one embodiment, the wearable, i.e, the mother unit may function without a mobile device connection. The wearable, i.e, the mother unit, may only have "outgoing data" function. In one embodiment the wearable i.e, the mother unit may communicate with other components such as wireless cameras, headphones, phones etc . . . , if necessary, that may be placed strategically on the equipment or worn by the user.

Figure 4:
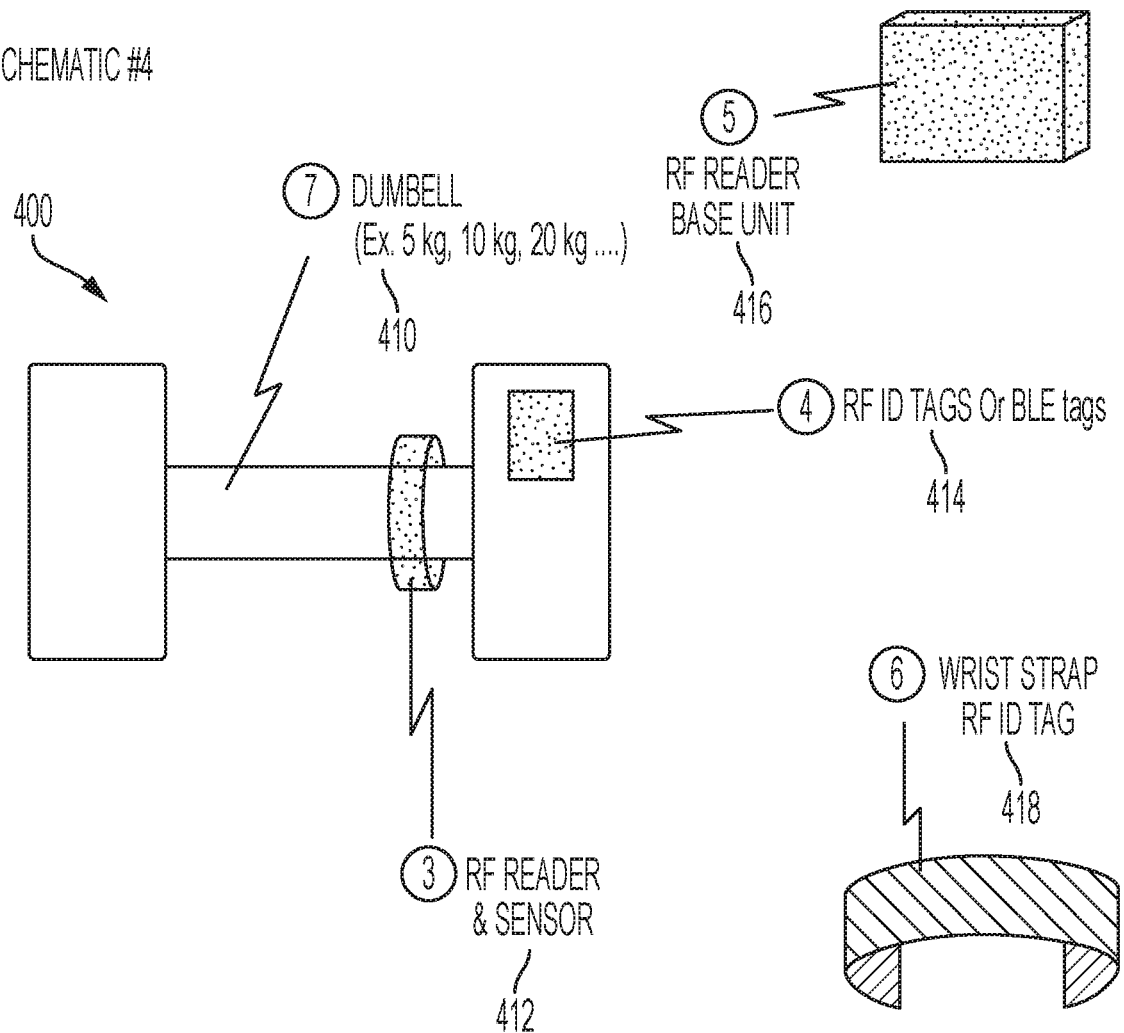
FIG. 4 illustrates an exemplary exercise tracker system, in accordance with an embodiment of the present invention.

In an exemplary embodiment, referring to FIG. 4 is illustrated an exemplary system 400 using an exercise tracker, in accordance with an embodiment of the present invention. FIG. 4 illustrates an exemplary embodiment of tracking the exercise routine of a user using a dumb-bell 410. The dumb-bell may be of any weight category like 5 kg, 10 kg, 20 kg, etc. . . . An RF ID reader and sensor 412 is placed at a convenient location as shown in FIG. 4, an tag 414 is placed on the dumb bell, a base unit 416 may be placed on a wall at a distance sufficient to receive and send RF signals to the RF ID reader and sensor 412, and a wearable with tag 418 may be provided to the user.

Figure 5:
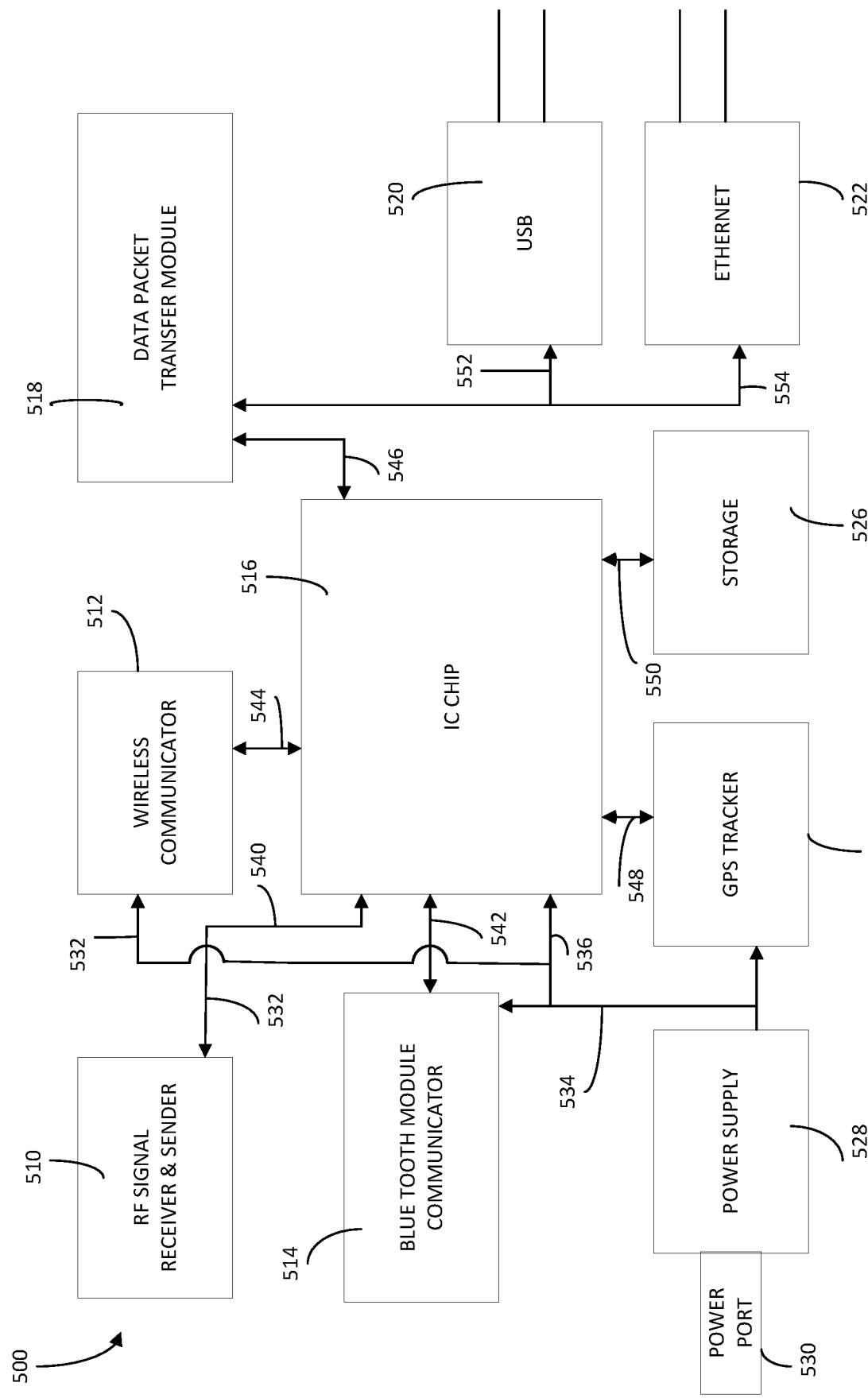
FIG. 5 is a block diagram illustrating an exemplary system of a component of an exercise tracker, in accordance with an embodiment of the present invention.

Referring to FIG. 5 is illustrated a block diagram 500 of one component of an exemplary exercise tracker system, in accordance with an embodiment of the present invention. FIG. 5 illustrates the sub-components of the RF reader base unit 500. In one exemplary embodiment, the RF reader base unit 500 may include but not be limited to, an RF signal receiver and sender 510, a wireless communicator 512, a Bluetooth® communicator 514 (optional), an IC chip 516, a data packet transfer module 518, ports for data transfer, for example a USB port 520, and ethernet port 522, a GPS tracker 524, database/data storage 526, and a power source 528. The IC chip 518 may be used to connect all above sub-components and coordinate all information before sending the information to the mother unit. The power source may be used to powers all internal components. The power supply may include but is not limited to a power supply port 530 or a battery.

As shown in FIG. 5 the power supply 528 may provide power supply 532 to the RF ID signal receiver and sender 510, power supply 534 to the Bluetooth® communicator 514; power supply 536 to the IC chip 516; power supply 538 to the wireless communicator 512, and power supply connections to the other sub-components in the figure (not indicated in figure). The IC chip 516 controls the sub-components via its connection to the sub-components; connection 540 for RF ID signal receiver and sender 510, connection 542 to the Bluetooth® communicator 514, connection 544 to the wireless communicator 512, connection 546 for data packet transfer module 518, connection 548 for GPS tracker 524, and connection 550 for storage 526. The data packet transfer module 518 is connected 552 to the USB port 520, and connected 554 to the ethernet port 522.

Figure 6:
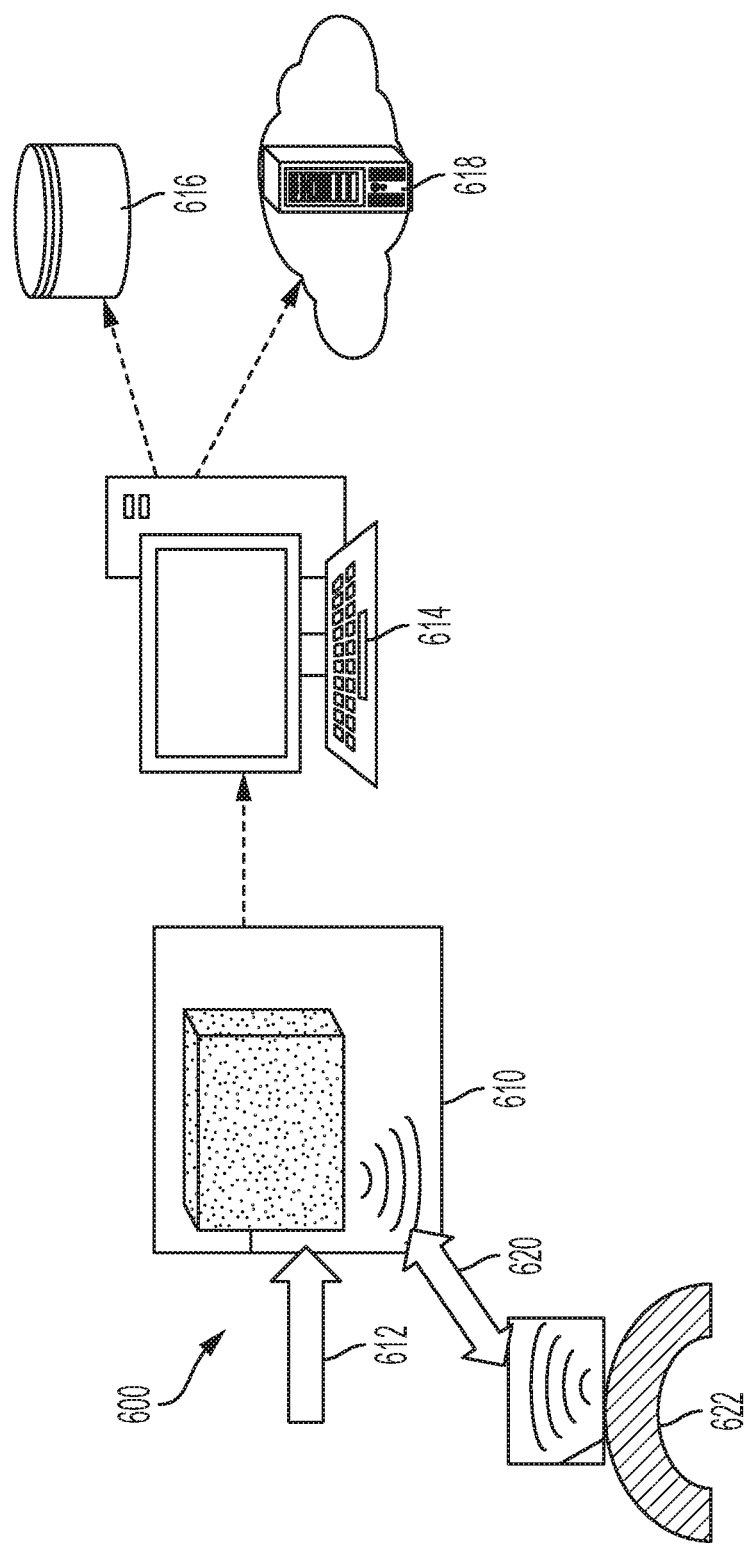
FIG. 6 illustrates an exemplary exercise tracker system, in accordance with an embodiment of the present invention.

Referring to FIG. 6 is illustrated a block diagram 600 of one component of an exemplary exercise tracker system, in accordance with an embodiment of the present invention. FIG. 6 illustrates the RF reader base unit 610 and its working. The RF reader base unit 610 may include a hub that may be physically connected to a computing system 614, a database 616, and a power source 612. The RF reader base unit 610 may include a wireless receiver that may track and receive data 620 to and from the RF reader and sensor 622. The RF reader base unit 610 may receive 620 data from RF Reader and Sensor 622 and store it in the database 616 that it may be connected to via the computing system 614. The data may include, but not be limited to, data from the 3-axis accelerometer, the 3-axis gyroscope, the altimeter, the voice recognition hardware, the timer, the counter, the tags on the equipment and the RF ID tags in the wearable. The IC chip may make a package of all the data and communicate the data to the RF reader base unit. The RF reader base unit may then send the data related to a user's gym routine, workout regimen, etc. . . . to the RF ID reader and sensor. The database 616 may include information on all users corresponding to their workouts and exercise routines. The computer 614 may also be connected to a server/cloud 618 and the information on the users corresponding to their workouts and exercise routines may be stored in the server/cloud 618. The users may access the information from the database/server/cloud. In one embodiment, the RF reader base unit may be placed on a wall and hence at times referred to as the base wall unit. It may be appreciated by a person with ordinary skill in the art, in light of and in accordance with the teachings of the present invention, that the RF reader base unit may be placed high enough to have clear connectivity, i.e., RF connectivity, wireless connectivity, bluetooth connectivity, and the like with the tags of all equipment and their corresponding RF readers and sensors, and RF ID tags in the wearable.

In one embodiment, the RF reader base unit may include a GPS tracking feature that enables the RF reader base unit to recognize a user via GPS tracking. In one embodiment, the GPS tracker may be contained in the wearable of the user. GPS coordinates may be used to identify the user's location and the RF reader base unit may then activate the mother unit, i.e., the RF reader and sensor on the equipment accordingly, for example, when a particular user enters the gym, the base unit would know that the particular user is in the gym and activate the user's profile in the RF reader and sensor.

It may be appreciated by a person with ordinary skill in the art, in light of and in accordance with the teachings of the present invention, a RF reader base unit 612 may be virtually any electronic device capable of receiving 620 data from a RF ID sensor and reader and transfer the data to a data base 616 via the computing system 614. The RF reader base unit 610 may include, but not be limited to, a wireless router capable of receiving/sending a signal from a computer to search the internet, and then send a signal to the service provider's server and the servers send data back to the wireless router.

It may be appreciated by a person with ordinary skill in the art, in light of and in accordance with the teachings of the present invention, the base unit 610 may connect to any number of devices with virtually any wired and/or wireless means. Base unit may connect to virtually any device by means such as, but not be limited to, Bluetooth connection, Ethernet cable, USB cable, WIFI, IRDA, RF, etc.

It may be appreciated by a person with ordinary skill in the art, in light of and in accordance with the teachings of the present invention, that a server 618 may be virtually any computing platform such as, but not limited to, a computer cluster, a laptop, a tablet, a smartphone, etc. . . . . It may be appreciated by a person with ordinary skill in the art, in light of and in accordance with the teachings of the present invention, that a database 616 may be virtually any data storage device or devices. Database 616 may include, but not be limited to, a plurality of data servers and a memory card. In another embodiment of the present invention, database 616 may be a memory card connected to server 618.

It may be appreciated by a person with ordinary skill in the art, in light of and in accordance with the teachings of the present invention, that database 616 may contain virtually any data to improve the functionality of the exercise tracker system 600. Database 616 may include, without limitation, exercise information, target goal libraries, equipment list, image databanks, user preferences, user routines, workout programs, etc. . . .

It may be appreciated by a person with ordinary skill in the art, in light of and in accordance with the teachings of the present invention that, exercise tracker system 600 may partially or completely contained in a local computing platform and/or network. In an alternative embodiment of the present invention, exercise tracker system 600 may be located on a local computer network.

Figure 7:
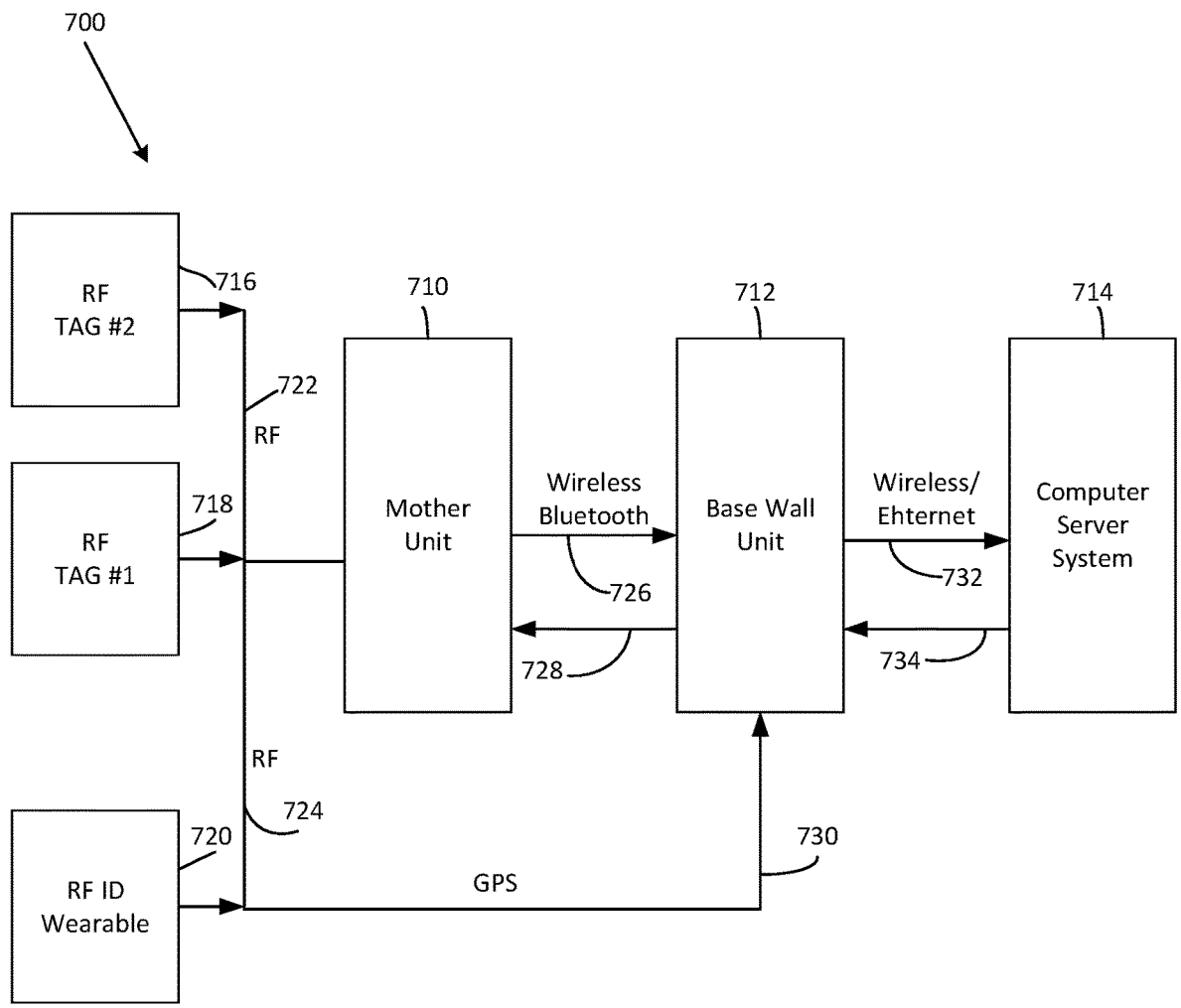
FIG. 7 illustrates an exemplary diagrammatic view of an exercise tracker system, in accordance with an embodiment of the present invention.

Referring to FIG. 7, is illustrated an exemplary diagrammatic view 700 of an exemplary exercise tracker system, in accordance with an embodiment of the present invention. The view 700 shows a mother unit 710, a base unit 712, and a computer system 714. The mother unit 710 receives data from the tags on an equipment 716, 718, and from the RF ID tags present in a user's wearable 720 via RF signals 722, 724. The mother unit 710 may communicate 726, 728 with the base unit 712 with reference to sending and receiving user information. The base unit 712 may receive 730 information on the user's location with the GPS tracker 720. The base unit 714 may communicate 732, 734 with the computer system 714 with reference to sending and receiving user information. In one exemplary embodiment, the tags 716, 718 may include active BLE tags or passive RF ID tags, transponder with information on the equipment, for example, information on weights, and the tags may be in the form of a sticker; the RF ID tags in the wearable and GPS tracker 720 may include active or passive RF ID tags, transponder with user ID, GPS chip for location and tracking the user within the gym, and may be in the form of a wearable, a key chain, a clip, etc . . . ; the mother unit 710 is the RF reader and sensor described with reference to FIG. 3, and may be considered as a wearable for an equipment; and the base unit 712 described with reference to FIG. 5 functions as a data consolidator, a hub between the mother unit and the computer system, and typically installed on an wall high enough for good connectivity to all the mother units.

Figure 8:
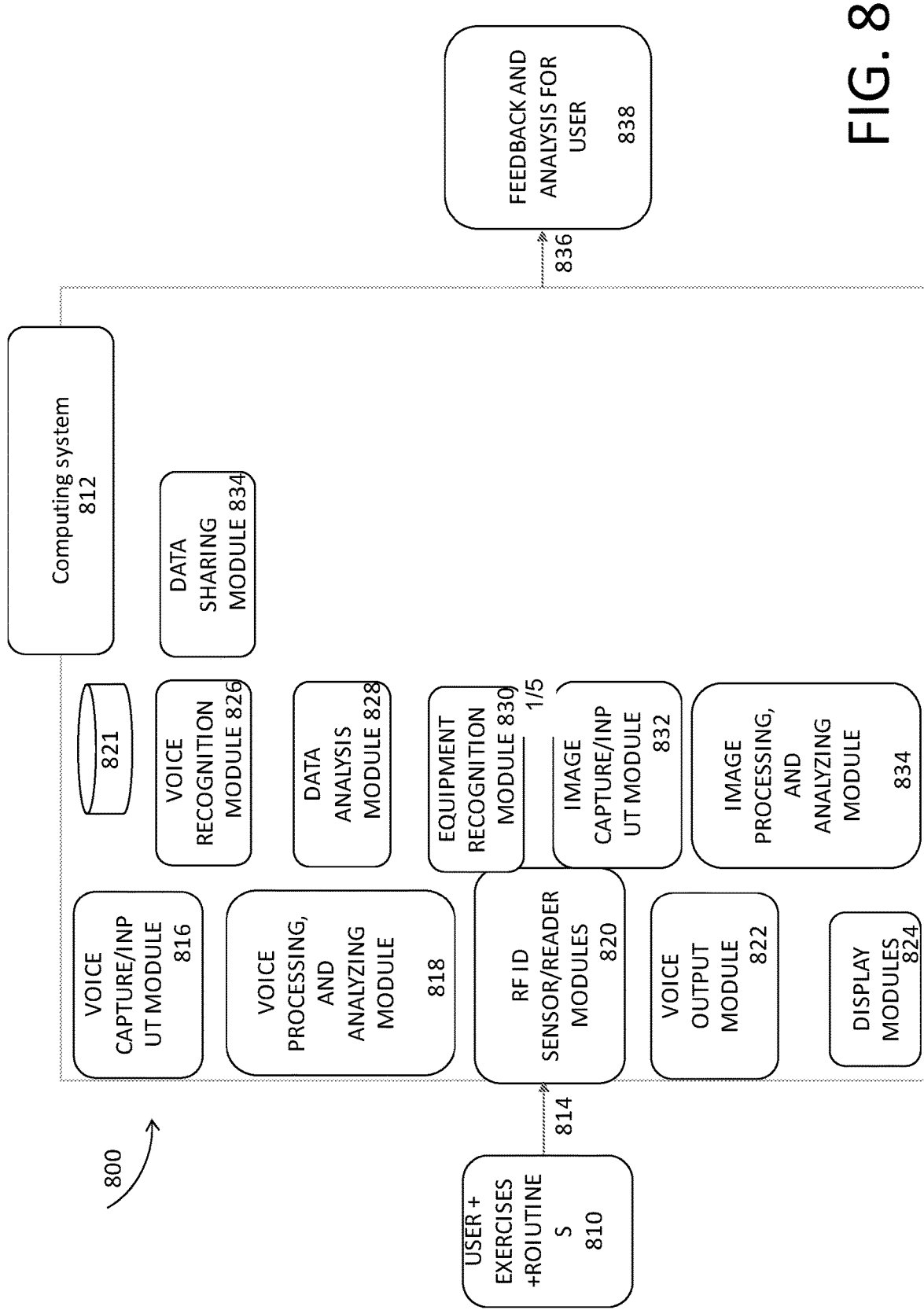
FIG. 8 illustrates an architecture of an exemplary exercise tracker system, in accordance with an embodiment of the present invention.

Referring to FIG. 8, is illustrated an architecture 800 of an exemplary exercise tracker system, in accordance with an embodiment of the present invention. An exercise tracker system architecture 800 may include a computing system 812. The computing system 812 provides the user an exercise tracking system, for example, as shown in FIG. 1, which enables the user to go through his/her exercise/routines 810 and get 836 a feedback/analysis 838. The computing system 812 may include a voice capture/input module 816, a voice processing and analyzing module 818, a RF ID reader and sensor module 820, a voice output module 822, a display module 824, a voice recognition module 826, a data analysis module 828, an equipment recognition module 828, an image capture/input module 830, an image processing and analyzing module 832, a database 821, and a data sharing module 834. Voice capture/input module 816 may have a means of capturing a voice of a user, such as, without limitation, sensors and/or a processing unit, and use it as input for the exercise tracker system for starting/capturing a user's routine once user selects an exercise/exercise equipment. Voice processing and analyzing module 818 may have a means of processing a voice such as, without limitation, a processing unit, a computer, or a server to execute computer code and/or algorithms from a non-transitory computer readable medium for voice recognition. RF ID reader and sensor module 820 may have a processing means such as, without limitation, a processing unit, a computer, or a server to execute computer code and/or algorithms from a non-transitory computer readable medium for sensing/detecting an RF ID and reading a RF signal. Voice output module 822 may have a processing means such as, without limitation, a processing unit, a computer, or a server to execute computer code and/or algorithms from a non-transitory computer readable medium for providing a voice output to the user. Display module 824 may have a processing means such as, without limitation, a processing unit, a computer, or a server to execute computer code and/or algorithms from a non-transitory computer readable medium for providing a display to the user. Voice recognition module 826 may have a processing means such as, without limitation, a processing unit, a computer, or a server to execute computer code and/or algorithms from a non-transitory computer readable medium for recognizing the voice of a user or the tap on the wearable. Data analysis module 828 may have a processing means such as, without limitation, a processing unit, a computer, or a server to execute computer code and/or algorithms from a non-transitory computer readable medium for providing an exercise data analysis to the user. equipment recognition module 828 may have a processing means such as, without limitation, a processing unit, a computer, or a server to execute computer code and/or algorithms from a non-transitory computer readable medium for recognizing the equipment selected by the user and resulting in the exercise routine capturing and analyzing data with relevance to the selected equipment. Image capture/input module 830 may have a processing means such as, without limitation, a processing unit, a computer, or a server to execute computer code and/or algorithms from a non-transitory computer readable medium for capturing an image of the user. Image processing and analyzing module 832 may have a processing means such as, without limitation, a processing unit, a computer, or a server to execute computer code and/or algorithms from a non-transitory computer readable medium for capturing, analyzing, and providing an image to the user. Data sharing module 834 may have a processing means such as, without limitation, a processing unit, a computer, or a server to execute computer code and/or algorithms from a non-transitory computer readable medium for sharing the data with the user or with social media on instructions of the user. All the modules may access one or more databases 821 as part of executing computer code and/or algorithms to provide the user with the necessary information for following through an exercise routine and achieving the intended goals.

It may be appreciated by a person with ordinary skill in the art, in light of and in accordance with the teachings of the present invention, that one or more modules may be embodied in a single device.

It may be appreciated by a person with ordinary skill in the art, in light of and in accordance with the teachings of the present invention, that virtually any algorithm and/or computer code may be used to recognize a voice on recognition module 826. Voice recognition algorithms and/or methods may include, without limitation, Bayesian networks, fuzzy logic, neural networks, template matching, Hidden Markov models, machine learning, data mining, feature extraction and data analysis/statistics, optical character recognition, etc. In an alternative embodiment of the present invention, a binary search tree may be implemented to extra data from an image.

It may be appreciated by a person with ordinary skill in the art, in light of and in accordance with the teachings of the present invention, that there may be a plurality of the same modules in the exercise tracker system architecture 800. A plurality of modules such as, without limitation, a voice capture/input module 816, a voice processing and analyzing module 818, a RF ID reader and sensor module 820, a voice output module 822, a display module 824, a voice recognition module 826, a data analysis module 828, an equipment recognition module 828, an image capture/input module 830, an image processing and analyzing module 832, a database 821, and a data sharing module 834 may be present in exercise tracker system architecture 800. The plurality of similar modules may work in parallel or independently to improve the throughput and/or speed of exercise tracker system architecture 800. In an alternative embodiment of the present invention, a plurality of modules may be connected to an exercise tracker system architecture 800 via wired and wireless connections to access resources from different wired and wireless networks. In still another alternative embodiment of the present invention, a plurality of similar modules may form a secondary exercise tracker system 800 capable of seamlessly substituting a messing and/or failing module.

It may be appreciated by a person with ordinary skill in the art, in light of and in accordance with the teachings of the present invention, that one or more modules may transmit exercise tracking/exercise machine tracking information to a tech support server that is on an accessible network or over the internet. In an alternative embodiment of the present invention, additional exercise tracking/exercise machine information may be sent to a server to alleviate processing load on an image-based problem correction system.

It may be appreciated by a person with ordinary skill in the art, in light of and in accordance with the teachings of the present invention, that any module in exercise tracker system architecture 800 may perform data manipulation. Data manipulation such as, but not limited to, compression, encryption, formatting. In an alternative embodiment of the present invention, any module sending data may first compress the data prior to data transmission.

Figure 9:
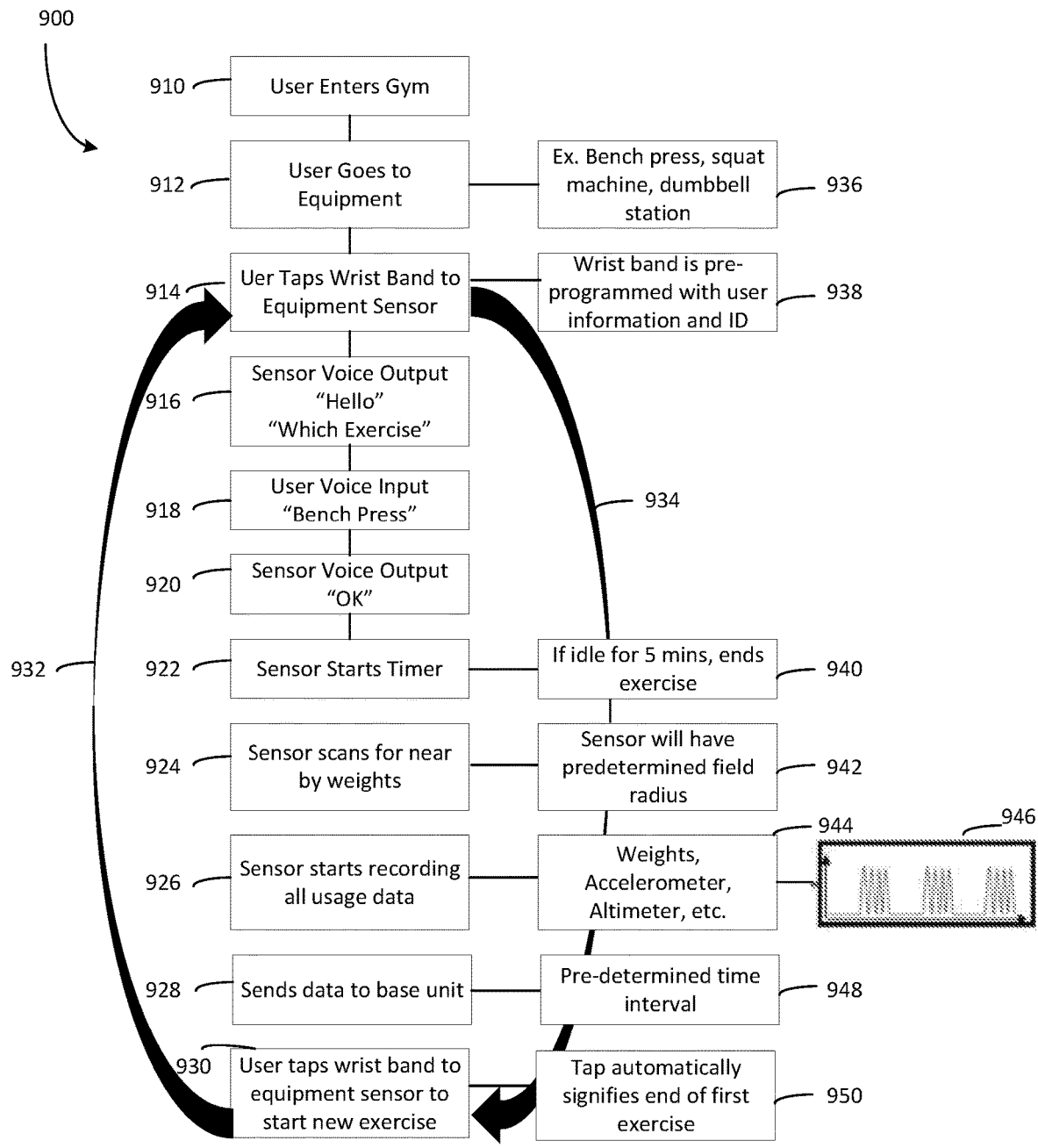
FIG. 9 illustrates an exemplary process using an exercise tracker system, in accordance with an embodiment of the present invention.

Referring to FIG. 9 is illustrated an exemplary process using an exercise tracker, in accordance with an embodiment of the present invention. In step 910 a user may enter a gym. In step 912 the user may approach an equipment, for example, the user may approach 936 a Bench press, squat machine, dumbbell station, etc. . . . . In step 914 the user may tap the wearable to the equipment sensor—RF ID sensor and reader, for example, a wristband. In one embodiment, the wearable may be pre-programmed 938 with user information and ID. In step 916 the RF ID reader and sensor provides a voice output to the user, for example, "hello" "which exercise". In step 918 the user may provide a voice input to the RF ID reader and sensor, for example, "bench press". In step 920 the RF ID reader and sensor provides a voice output response to the user, for example, "OK". In step 922 the RF ID reader and sensor may start the timer. In one embodiment, the timer may be pre-programmed, for example, if the timer determines 940 an idle time of about 5 minutes the timer may signal/direct the mother unit, i.e., the RF reader and sensor. The RF reader and sensor may send a signal to the IC chip which may then stop tracking data on all other components described herein above, to end the exercise. In a next step 924 the RF ID reader and sensor will scan for nearby weights. The sensor may have a pre-determined field radius 942. It may be appreciated by a person with ordinary skill in the art, in light of and in accordance with the teachings of the present invention, that the RF reader and sensor may include a near field Bluetooth reader, a near free RF ID reader, or a combination thereof. The near field Bluetooth reader or RF ID reader may be programmed to read BLE tags or RF ID tags, respectively in a particular pre-determined filed radius. The radius may be substantially small i.e., extremely right and may allow the RF reader and sensor to sense only the tags on an exercise equipment, for example, the tags placed on the weights that may be placed on the bench press bar. The RF reader and sensor is enabled to track the exercises using the components within it, as described with reference to FIG. 3. For example, the 3-axis accelerometer may track movement. The data may be encoded to summarize the repetitions. The RF ID reader and sensor, is enabled to add this data only to user's profile, who has tapped the sensor with their wearable i.e., brought the wearable in physical contact with the RF ID reader and sensor on the exercise equipment. In step 926 the RF ID reader and sensor starts recording all usage data 944, i.e., weights, accelerometer, altimeter etc. . . . and may provide a data output 946. In step 928 the RF ID reader and sensor may send the usage data i.e., data output 946 in its raw form to the RF reader base unit. The RF reader base unit in turn may send the data to the computer system in the exercise tracker system to get decoded, analyzed, and stored against the respective user's in their user profile.

The usage data may be sent 948 at pre-determined time intervals. In step 930 user may tap the wearable to equipment sensor to start new exercise and the steps 914-930 may be repeated 932,934.

Other useful design variations, different form factors for the RF reader base unit, the RF ID reader and sensor, and the tags. In one embodiment, the RF reader base unit may include a box of any shape suitable to house all the components. In various embodiments, the RF ID reader and sensor and the tags may be in the form of a sticker, an embedded micro-chip, a circular band to a key chain, and the like.

The designated computer program may be enabled to use the components inside of the modules, for example, use the components 3-axis accelerometer, 3-axis gyroscope, altimeter, microphone, speaker, etc. . . . in a RF ID reader and sensor. Accordingly, the designate software program may collect data from the modules and use it to give the user the features described herein above. In one embodiment, parts of the designated computer program may be installed in each module based on their functionality and requirements. In one exemplary embodiment, the tags on the equipment may include weight and/or equipment information programmed in the transponder. In one exemplary embodiment, the RF ID tags on the wearable may include user ID programmed in the transponder and GPS module and designated computer program for GPS tracking. The user ID may be re-programmed when needed, for example, when the wearable may be assigned to different users. In one embodiment, the RF ID reader and sensor, i.e., the mother unit may include designated computer programs for connectivity i.e., wireless, Bluetooth®, RF, and the like, for data collection, for data transfer (wireless and wired), for providing pre-programmed messages and commands, for audio/input out and receiving signal from RF reader base unit, for data storage, and the like. In one embodiment, the data storage may have a capacity in a range of from about 8 KB-1024 MB. In one embodiment, the RF reader base wall unit may include designated computer programs for connectivity i.e., wireless, Bluetooth®, RF, and the like, for data gathering from all mother units i.e., the RF reader and sensor units in the gym, for data transferring (wireless and wired), for GPS tracking, for data transfer to and from server and computer system, and for data storage, for example, to store data of all active users inside the gym at a given time. The GPS tracking in the RF may activate the storage feature. The RF reader base unit may then download the user's profile/data i.e., the exercise routine, music, past data and trends, etc. . . . from the database/server and use it to communicate with the user via the RF ID reader and sensor. The computer system and server may include designated computer program for data analysis, for user interface i.e., website, mobile application etc . . . , for exercise analysis input and output i.e., personal trainer, correct technique, proper form, etc . . . , for storing user data using user input (music, custom messages, etc. . . . and for storing data collected by the exercise tracker system described herein. In one embodiment, the exercise tracker system and process described herein may provide a statistical analysis of the user's workout routine. As shown in FIG. 2 the four components described herein track user and equipment movement and all necessary information for the user's activity and provide information on 1) number of sets, 2) number of repetitions, 3) amount of weights being used for each rep/set, 4) number of exercise equipment, etc. . . .

In one embodiment, the exercise tracker system and process described herein may recognize pre-installed exercises that are being performed by the same user, for example, bench-press, squats, deadlifts, etc. . . .

In one embodiment, the exercise tracker system and process described herein may enable the user to use their voice to let the system know about which exercise they are performing for the exercises that are not recognized by the exercise tracker system. In one embodiment, the user may provide an input message to the mother unit i.e., the RF reader and sensor. The user may provide a voice command to the RF reader and sensor and mention the exercise, for example, "Barbell Fly". The RF reader and sensor in turn may send the corresponding data to the RF reader base unit. The RF reader base unit may then send the data to the computer system for analysis and assimilation either real time or post processing.

In one embodiment, the exercise tracker system and process described herein may function as a personal trainer for the user. The designated computer algorithm/program may be designed in a way that allows the user's data to be used to generate future training routines, i.e., the designated computer algorithm may have heuristic capabilities. This may either be done by the gym owners, their human personal trainers or the designated computer algorithm provider. In one embodiment, a user may opt for an option where the in-house personal trainer loads up routines onto the system (in the user's account) and the exercise tracker system modules will take care of letting the user know which exercise to do and how many of each. In an alternative embodiment, the user may cultivate their own routine in a user portal (on the internet). In one embodiment, though this may require user input, it is not mandatory for the functioning of the system. In one embodiment, the user may have a history of the amount of weights they used in the past and what they need to use in the future. The exercise tracker system may enable track this information. In certain embodiments, the exercise tracker system the module can access their records and notify the user when they exceed their previous best or when they reach their 1 Rep Maximum, etc. . . .

Since each equipment may have its own module, and may be capable of recognizing the user, the module may have access to the user's previous data. based on this data, the module may be capable of functioning as the user's personal trainer by recommending the number of sets, and reps they should do for each exercise. For example, Day 1: a user comes and does 4 sets of bench press @ 20 KG, 25 KG, 30 KG, 35 KG. The next time the user wants to do a bench press the module may be able to recommend a new weight or set for the user. The data may be provided from the computer system via the RF reader base unit. Once the RF reader base unit recognizes the user, the RF reader base unit may download the user information from the server/database and send it to the RF reader and sensor, i.e., the mother unit, and the mother unit may provide the information to the user.

In one embodiment, the exercise tracker system and process described herein may allow the gym owner to track their equipment usage. Each module of the RF reader and sensor may know how many reps/sets has been performed on it. The data may be sent to the server/database via the RF reader base unit and the gym owners may have their own portal with access to the usage data. This data may help the gym owner to recognize their popular equipment, the wear and tear on each equipment and hence they may plan the maintenance schedules based on this information.

In one embodiment, the exercise tracker system and process described herein may enable the RF reader and sensor modules on the equipment to give motivational messages to the user when lifting. For example: when the user is doing a squat and the RF reader and sensor module recognizes the active exercise the module may motivate the user by giving them messages like "You can do it", "One more Rep", "Almost there" etc. . . . . These messages may be pre-installed in the memory/storage of the RF reader and sensor modules.

It may be appreciated by a person with ordinary skill in the art, in light of and in accordance with the teachings of the present invention, that either the user or the gym owner may register the user and provide the user with a login id and password for the exercise tracker system described herein. In one embodiment, the exercise tracker system and process described herein may also allow the user to build a playlist in their account. This playlist may be stored in the database and may be accessed directly by the user when they are in the gym. The RF reader and sensor modules may be connected to the database (via the RF reader base unit) and can access the playlist. The RF reader and sensor modules may connect to a Bluetooth headphone and will be able to stream the music to the user. The user may not have to carry any other mobile device to play their music. They may need only their headphones.

In one embodiment, the exercise tracker system and process described herein may enable the user to connect to their mobile device via the RF reader and sensor modules on the equipment via Bluetooth and take pictures of the user while they exercise. This may require strategic placement of the mobile device on the equipment. In one embodiment, this feature may be provided by gym owner. The designated software algorithm may enable the mobile device to click the picture at a particular moment, for example, half way through a rep, uphill of a squat, or bench press, etc. . . . . In one embodiment, the user may direct the RF reader and sensor module to take a picture when they choose by simply saying "take picture".

In one embodiment, the exercise tracker system and process described herein may enable a user share his/her information on the social media (WEB PORTAL) i.e., once the user logs in to their account/portal on the internet, they may be given the option to share their workout data with social websites. For example, today's workout, todays max weights, next week's plans etc. .... The web portal may also be used to hold competitions between users, share exercise tips, share exercise regiments, and the like.

In one embodiment, the responsibility of charging and maintaining the exercise tracker system may be transferred to the gym owner. In certain embodiments, if the gym is at a user's home, the user may have to carry out the additional responsibilities of a gym owner as described hereinabove, i.e., maintainer charge for all devices, etc. . . .

In one exemplary embodiment, the exercise tracker system may include these components. The base unit (RF reader base unit), the mother unit (RF ID reader and sensor), tags, RF ID wearable, and a computer system. During a typical working of the exercise tracker system, these components may be constantly communicating with each other via various forms of connectivity methods. Generally the mother unit, i.e., the RF ID reader and sensor, may be the central focus point. It may have all the fancy wearable tech that is required to track the users workout. The wearables may be placed on the equipment and not worn by the user. The RF ID reader sensor unit may have other features including, but not be limited to 1) microphone, 2) speaker, and 3) RF ID tag reader. The microphone enables the user to talk to the unit. The speaker enables the unit to talk back to the user. The RF ID reader i.e., the mother unit will communicate with the the tags. These tags may be placed on loose weights and moveable parts in the gym. For examples, the mother unit would be placed on a barbell, but the tags would be placed on the weights that go along with a barbell. When in proximity (programmed via software), the mother unit may sense the tags and will recognize its use. This may communicate to the RF ID reader and sensor unit of the users weight usage. The mother unit will then output this data to the base unit. The base unit may then record the data in a database using the designated computer program. This is the basic working model. Each gym would have multiple mother units and multiple tags, but only 1-2 base unit that would talk to all mother units simultaneously (outlined in the software patent). The mother unit may be capable of connecting to other mobile devices, headphones or cameras and allowed the user to use them via the microphone/ bluetooth feature. The base and mother units may recognize a particular user because the user may also posses some sort of RF ID tag wearable given to them by the gym or integrated into a personal item (based on their choice). When a user comes in close proximity to the mother unit, it would recognise the user and accumalate all useage data under their name. The base unit may be alerted on the user via the GPS tracker.

In one embodiment, the exercise tracker system and process described herein may have various advantages. The advantages include, but are not limited to, (i) the exercise tracker system being equipment based and not user based as all sensors may be attached onto the equipment directly; (ii) the exercise tracker system being voice activated resulting in an almost hands-free exercise starting process; (iii) BLE Tag connectivity; (iv) RF ID Tag connectivity; among others.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Figure 10:
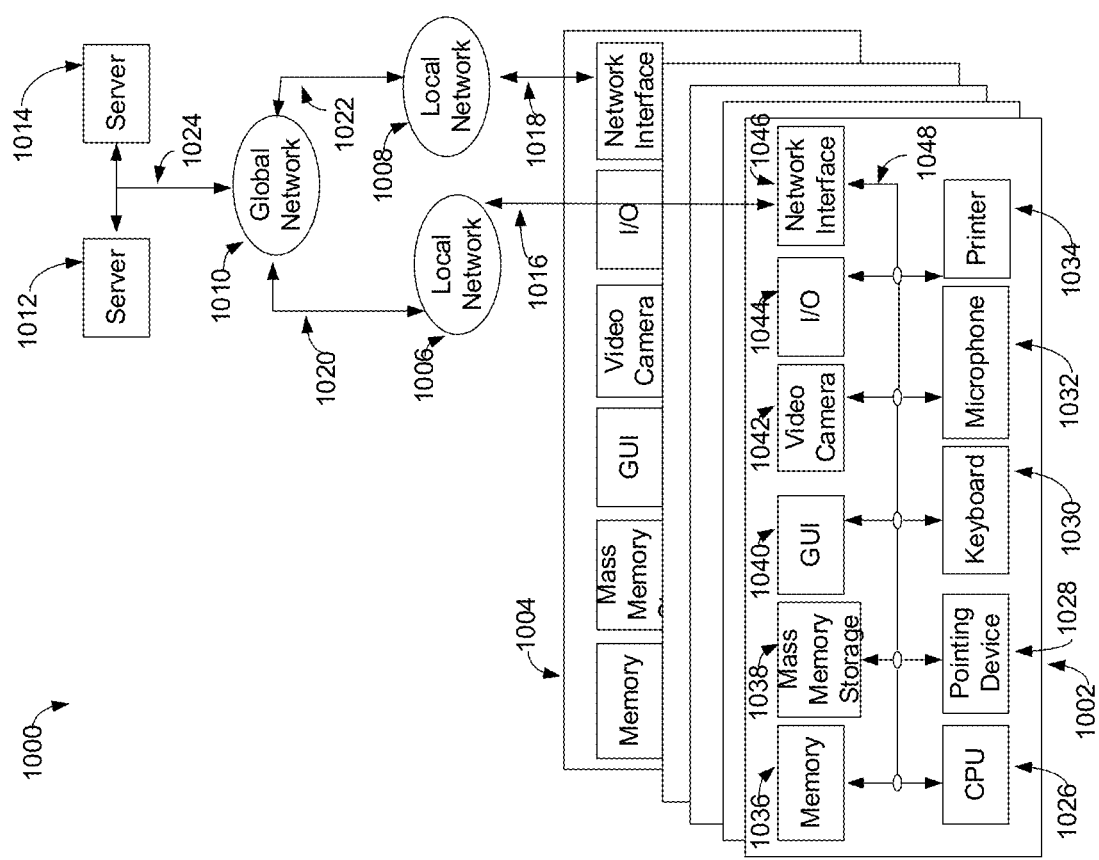
FIG. 10 is a block diagram depicting an exemplary client/server system which may be used by an exemplary web-enabled/networked embodiment of the present invention.

FIG. 10 is a block diagram depicting an exemplary client/server system which may be used by an exemplary web-enabled/networked embodiment of the present invention.

A communication system 1000 includes a multiplicity of clients with a sampling of clients denoted as a client 1002 and a client 1004, a multiplicity of local networks with a sampling of networks denoted as a local network 1006 and a local network 1008, a global network 1010 and a multiplicity of servers with a sampling of servers denoted as a server 1012 and a server 1014.

Client 1002 may communicate bi-directionally with local network 1006 via a communication channel 1016. Client 1004 may communicate bi-directionally with local network 1008 via a communication channel 1018. Local network 1006 may communicate bi-directionally with global network 1010 via a communication channel 1020. Local network 1008 may communicate bi-directionally with global network 1010 via a communication channel 1022. Global network 1010 may communicate bi-directionally with server 1012 and server 1014 via a communication channel 1024. Server 1012 and server 1014 may communicate bi-directionally with each other via communication channel 1024. Furthermore, clients 1002, 1004, local networks 1006, 1008, global network 1010 and servers 1012, 1014 may each communicate bi-directionally with each other.

In one embodiment, global network 1010 may operate as the Internet. It will be understood by those skilled in the art that communication system 1000 may take many different forms. Non-limiting examples of forms for communication system 1000 include local area networks (LANs), wide area networks (WANs), wired telephone networks, wireless networks, or any other network supporting data communication between respective entities.

Clients 1002 and 1004 may take many different forms. Non-limiting examples of clients 1002 and 1004 include personal computers, personal digital assistants (PDAs), cellular phones and smartphones.

Client 1002 includes a CPU 1026, a pointing device 1028, a keyboard 1030, a microphone 1032, a printer 1034, a memory 1036, a mass memory storage 1038, a GUI 1040, a video camera 1042, an input/output interface 1044, and a network interface 1046.

CPU 1026, pointing device 1028, keyboard 1030, microphone 1032, printer 1034, memory 1036, mass memory storage 1038, GUI 1040, video camera 1042, input/output interface 1044 and network interface 1046 may communicate in a unidirectional manner or a bi-directional manner with each other via a communication channel 1048. Communication channel 1048 may be configured as a single communication channel or a multiplicity of communication channels.

CPU 1026 may be comprised of a single processor or multiple processors. CPU 1026 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 1036 is used typically to transfer data and instructions to CPU 1026 in a bi-directional manner. Memory 1036, as discussed previously, may include any suitable computer-readable media, intended for data storage, such as those described above excluding any wired or wireless transmissions unless specifically noted. Mass memory storage 1038 may also be coupled bi-directionally to CPU 1026 and provides additional data storage capacity and may include any of the computer-readable media described above. Mass memory storage 1038 may be used to store programs, data and the like and is typically a secondary storage medium such as a hard disk. It will be appreciated that the information retained within mass memory storage 1038, may, in appropriate cases, be incorporated in standard fashion as part of memory 1036 as virtual memory.

CPU 1026 may be coupled to GUI 1040. GUI 1040 enables a user to view the operation of computer operating system and software. CPU 1026 may be coupled to pointing device 1028. Non-limiting examples of pointing device 1028 include computer mouse, trackball and touchpad. Pointing device 1028 enables a user with the capability to maneuver a computer cursor about the viewing area of GUI 1040 and select areas or features in the viewing area of GUI 1040. CPU 1026 may be coupled to keyboard 1030. Keyboard 1030 enables a user with the capability to input alphanumeric textual information to CPU 1026. CPU 1026 may be coupled to microphone 1032. Microphone 1032 enables audio produced by a user to be recorded, processed and communicated by CPU 1026. CPU 1026 may be connected to printer 1034. Printer 1034 enables a user with the capability to print information to a sheet of paper. CPU 1026 may be connected to video camera 1042. Video camera 1042 enables video produced or captured by user to be recorded, processed and communicated by CPU 1026.

CPU 1026 may also be coupled to input/output interface 1044 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 1026 optionally may be coupled to network interface 1046 which enables communication with an external device such as a database or a computer or telecommunications or internet network using an external connection shown generally as communication channel 1016, which may be implemented as a hardwired or wireless communications link using suitable conventional technologies. With such a connection, CPU 1026 might receive information from the network, or might output information to a network in the course of performing the method steps described in the teachings of the present invention.

Figure 11:
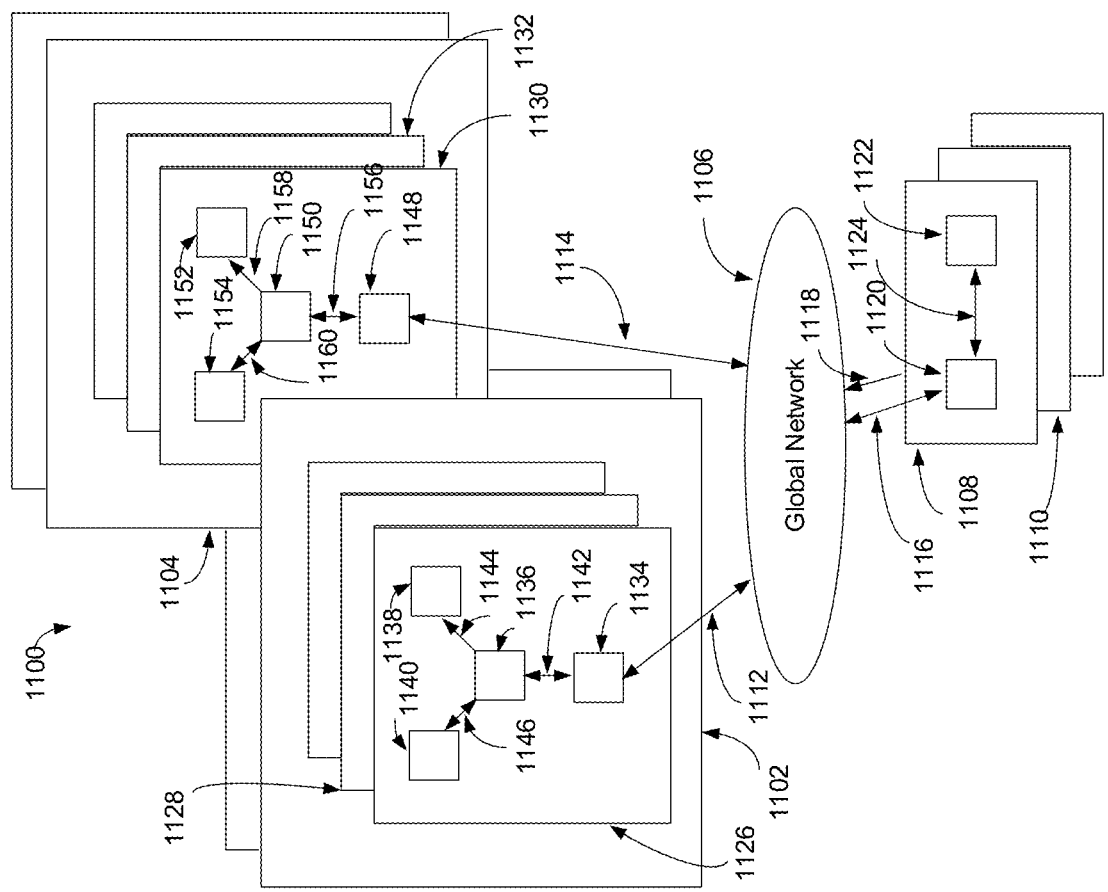
FIG. 11 illustrates a block diagram depicting a conventional client/server communication system.

FIG. 11 illustrates a block diagram depicting a conventional client/server communication system.

A communication system 1100 includes a multiplicity of networked regions with a sampling of regions denoted as a network region 1102 and a network region 1104, a global network 1106 and a multiplicity of servers with a sampling of servers denoted as a server device 1108 and a server device 1110.

Network region 1102 and network region 1104 may operate to represent a network contained within a geographical area or region. Non-limiting examples of representations for the geographical areas for the networked regions may include postal zip codes, telephone area codes, states, counties, cities and countries. Elements within network region 1102 and 1104 may operate to communicate with external elements within other networked regions or within elements contained within the same network region.

In some implementations, global network 1106 may operate as the Internet. It will be understood by those skilled in the art that communication system 1100 may take many different forms. Non-limiting examples of forms for communication system 1100 include local area networks (LANs), wide area networks (WANs), wired telephone networks, cellular telephone networks or any other network supporting data communication between respective entities via hardwired or wireless communication networks. Global network 1106 may operate to transfer information between the various networked elements.

Server device 1108 and server device 1110 may operate to execute software instructions, store information, support database operations and communicate with other networked elements. Non-limiting examples of software and scripting languages which may be executed on server device 1108 and server device 1110 include C, C++, C # and Java.

Network region 1102 may operate to communicate bi-directionally with global network 1106 via a communication channel 1112. Network region 1104 may operate to communicate bi-directionally with global network 1106 via a communication channel 1114. Server device 1108 may operate to communicate bi-directionally with global network 1106 via a communication channel 1116. Server device 1110 may operate to communicate bi-directionally with global network 1106 via a communication channel 1118. Network region 1102 and 1104, global network 1106 and server devices 1108 and 1110 may operate to communicate with each other and with every other networked device located within communication system 1100.

Server device 1108 includes a networking device 1120 and a server 1122. Networking device 1120 may operate to communicate bi-directionally with global network 1106 via communication channel 1116 and with server 1122 via a communication channel 1124. Server 1122 may operate to execute software instructions and store information.

Network region 1102 includes a multiplicity of clients with a sampling denoted as a client 1126 and a client 1128. Client 1126 includes a networking device 1134, a processor 1136, a GUI 1138 and an interface device 1140. Non-limiting examples of devices for GUI 1138 include monitors, televisions, cellular telephones, smartphones and PDAs (Personal Digital Assistants). Non-limiting examples of interface device 1140 include pointing device, mouse, trackball, scanner and printer. Networking device 1134 may communicate bi-directionally with global network 1106 via communication channel 1112 and with processor 1136 via a communication channel 1142. GUI 1138 may receive information from processor 1136 via a communication channel 1144 for presentation to a user for viewing. Interface device 1140 may operate to send control information to processor 1136 and to receive information from processor 1136 via a communication channel 1146. Network region 1104 includes a multiplicity of clients with a sampling denoted as a client 1130 and a client 1132. Client 1130 includes a networking device 1148, a processor 1150, a GUI 1152 and an interface device 1154. Non-limiting examples of devices for GUI 1138 include monitors, televisions, cellular telephones, smartphones and PDAs (Personal Digital Assistants). Non-limiting examples of interface device 1140 include pointing devices, mousse, trackballs, scanners and printers. Networking device 1148 may communicate bi-directionally with global network 1106 via communication channel 1114 and with processor 1150 via a communication channel 1156. GUI 1152 may receive information from processor 1150 via a communication channel 1158 for presentation to a user for viewing. Interface device 1154 may operate to send control information to processor 1150 and to receive information from processor 1150 via a communication channel 1160.

For example, consider the case where a user interfacing with client 1126 may want to execute a networked application. A user may enter the IP (Internet Protocol) address for the networked application using interface device 1140. The IP address information may be communicated to processor 1136 via communication channel 1146. Processor 1136 may then communicate the IP address information to networking device 1134 via communication channel 1142. Networking device 1134 may then communicate the IP address information to global network 1106 via communication channel 1112. Global network 1106 may then communicate the IP address information to networking device 1120 of server device 1108 via communication channel 1116. Networking device 1120 may then communicate the IP address information to server 1122 via communication channel 1124. Server 1122 may receive the IP address information and after processing the IP address information may communicate return information to networking device 1120 via communication channel 1124. Networking device 1120 may communicate the return information to global network 1106 via communication channel 1116. Global network 1106 may communicate the return information to networking device 1134 via communication channel 1112. Networking device 1134 may communicate the return information to processor 1136 via communication channel 1142. Processor 1146 may communicate the return information to GUI 1138 via communication channel 1144. User may then view the return information on GUI 1138.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6). In some embodiments, the methods and/or system components which may be located and/or performed remotely include, without limitation:

It is noted that according to USA law, all claims must be set forth as a coherent, cooperating set of limitations that work in functional combination to achieve a useful result as a whole. Accordingly, for any claim having functional limitations interpreted under 35 USC § 112 (6) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6) is/(are) dependent on one or more remote servers located outside the USA, it is intended that each such recited function under 35 USC § 112 (6) is to be interpreted as the function of the local system receiving the remotely generated information required by a locally implemented claim limitation, wherein the structures and or steps which enable, and breath life into the expression of such functions claimed under 35 USC § 112 (6) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present application, and "35 USC § 112 (6)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing the exercise tracker apparatus according to the present invention will be apparent to those skilled in the art. Various aspects of the invention have been described above by way of illustration, and the specific embodiments disclosed are not intended to limit the invention to the particular forms disclosed. The particular implementation of the exercise tracker system may vary depending upon the particular context or application. By way of example, and not limitation, the exercise tracker apparatus described in the foregoing were principally directed to tracking of a user's exercise machine usage, workout, and routine; however, similar techniques may instead be applied to sporting events to track sportsperson data, to track whereabouts of kids at school, to track whereabouts of employees in an office, and the like, and may be extended to include artificial intelligence which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

The invention claimed is:

1. A method comprising the steps of:
   providing an apparatus, wherein the apparatus comprises:
   at least one mother unit, wherein the mother unit comprises a radio frequency reader and sensor, an antenna, 3-axis accelerometer, 3-axis gyroscope, an altimeter, a short range wireless interconnection module, a wireless module, an integrated circuit chip, a microphone, a speaker, a voice recognition module, a power source, a data storage, and a counter/timer, wherein the mother unit is joined to an equipment in a gym;
   at least one equipment tag, wherein the equipment tag is placed on the equipment, wherein the at least one equipment tag is a radio frequency equipment tag or a short range wireless interconnection equipment tag, wherein the at least one equipment tag is in communication with the mother unit;
   at least one base unit, wherein the base unit comprises a radio frequency identification reader, a short range wireless interconnection module, a wireless module, an integrated circuit chip, global positioning system module, wherein a plurality of mother units is in communication with the base unit;

at least one radio frequency and global positioning system enabled user tag, wherein the radio frequency and global positioning system enabled user tag is joined to a user in the gym, wherein the radio frequency and global positioning system enabled user tag is in communication with the mother unit;

wherein the apparatus is a substantially hands-free and substantially automated exercise tracking apparatus; and providing the at least one radio frequency user tag to a user entering the gym;

registering a user profile;

capturing, by the mother unit user exercise data of an exercise equipment;

providing a computer system in communication with the base unit;

communicating the user exercise data captured by the mother unit to the computer system via the base unit;

analyzing, by the computer system the user exercise data and generating a feedback for the user; and communicating the feedback to the mother unit, by the computer system via the base unit; and communicating the feedback to the user via the mother unit.

2. The method of claim 1, wherein the mother unit comprises a radio frequency identification reader, an antenna, a 3-axis accelerometer, an altimeter, a voice recognition hardware, a microphone, a speaker, an integrated circuit chip, a counter/timer, a wireless communicator, and a database.

3. The method of claim 1, wherein the 3-axis accelerometer and 3-axis gyroscope is used to measure the motion characteristics of the equipment.

4. The method of claim 1, wherein the altimeter is used to measure the altitude of the equipment to identify the exercise being performed.

5. The method of claim 1, wherein the radio frequency identification reader and antenna are used to decipher and execute a voice command provided by the user.

6. The method of claim 1, wherein the voice recognition hardware, the microphone, and the speaker used to decipher and execute a tap command provided by the user.

7. The method of claim 1, wherein the counter/timer is used synchronously with the 3-axis accelerometer to track the exercise performed by a user.

8. The method of claim 1, further comprising a power source.

9. The method of claim 1, wherein the at least one Bluetooth Beacon equipment tag is joined to the equipment at a pre-determined distance to the mother unit.

10. The method of claim 1, wherein the base unit is placed in a position in a gym such that the base unit is in communication with the plurality of mother units in the gym.

11. The method of claim 1, wherein the base unit comprises a radio frequency signal receiver and sender, a wireless communicator, an integrated circuit chip, a GPS tracker, data packet transfer module, a database, and a power source.

12. The method of claim 1, wherein the radio frequency user tag is passive or active.

13. The method of claim 1, wherein the mother unit is in communication with an external device selected from an external device consisting of: a camera, a head phone, and a mobile phone.

14. The method of claim 13, wherein the external device is placed on the equipment or on the user.

15. The method of claim 14, wherein the external device enables the user to share user exercise data.

16. The method of claim 1, wherein the mother unit is enabled to provide motivational messages to the user.

17. The method of claim 1, wherein the mother unit is an equipment wearable that is enabled to send user, equipment, and exercise data to the base unit.

18. A system comprising:

an apparatus, wherein the apparatus comprises:

at least one mother unit, wherein the mother unit comprises a radio frequency reader and sensor, an antenna, 3-axis accelerometer, 3-axis gyroscope, an altimeter, a short range wireless interconnection module, a wireless module, an integrated circuit chip, a microphone, a speaker, a voice recognition module, a power source, a data storage, and a counter/timer, wherein the mother unit is joined to an equipment in a gym;

at least one equipment tag, wherein the equipment tag is placed on the equipment, wherein the at least one equipment tag is a radio frequency equipment tag or a short range wireless interconnection equipment tag, wherein the at least one equipment tag is in communication with the mother unit;

at least one base unit, wherein the base unit comprises a radio frequency identification reader, a short range wireless interconnection module, a wireless module, an integrated circuit chip, global positioning system module, wherein a plurality of mother units is in communication with the base unit;

at least one radio frequency and global positioning system enabled user tag, wherein the radio frequency and global positioning system enabled user tag is joined to a user in the gym, wherein the radio frequency and global positioning system enabled user tag is in communication with the mother unit;

wherein the apparatus is a substantially hands-free exercise tracking apparatus; and a computer system in communication with the base unit, wherein the computer system is enabled to analyze user exercise data and provide feedback to the user via the base unit and the mother unit; and wherein the system is a substantially hands-free and substantially automated exercise tracking system.

19. A non-transitory computer-readable storage medium with an executable program stored thereon, wherein the program instructs one or more processors to perform the following steps:

at least one mother unit, wherein the mother unit comprises a radio frequency reader and sensor, an antenna, 3-axis accelerometer, 3-axis gyroscope, an altimeter, a short range wireless interconnection module, a wireless module, an integrated circuit chip, a microphone, a speaker, a voice recognition module, a power source, a data storage, and a counter/timer, wherein the mother unit is joined to an equipment in a gym;

at least one equipment tag, wherein the equipment tag is placed on the equipment, wherein the at least one equipment tag is a radio frequency equipment tag or a short range wireless interconnection equipment tag, wherein the at least one equipment tag is in communication with the mother unit;

at least one base unit, wherein the base unit comprises a radio frequency identification reader, a short range wireless interconnection module, a wireless module, an integrated circuit chip, global positioning system module, wherein a plurality of mother units is in communication with the base unit;

at least one radio frequency and global positioning system enabled user tag, wherein the radio frequency and global positioning system enabled user tag is joined to a user in the gym, wherein the radio frequency and global positioning system enabled user tag is in communication with the mother unit;

wherein the apparatus is a substantially hands-free and substantially automated exercise tracking apparatus; and providing the at least one radio frequency user tag to a user entering the gym;

registering a user profile;

capturing, by the mother unit user exercise data of an exercise equipment;

providing a computer system in communication with the base unit;

communicating the user exercise data captured by the mother unit to the computer system via the base unit;

analyzing, by the computer system the user exercise data and generating a feedback for the user; and communicating the feedback to the mother unit, by the computer system via the base unit; and communicating the feedback to the user via the mother unit.

* * * * *